US009949900B2

(12) United States Patent
Lee et al.

(10) Patent No.: US 9,949,900 B2
(45) Date of Patent: Apr. 24, 2018

(54) METHOD FOR PREPARING MULTILAYER LAMELLAR LIQUID CRYSTAL EMULSION INCLUDING INTERCELLULAR LIPIDS

(71) Applicant: COSMAX CO., LTD., Hwaseong-si (KR)

(72) Inventors: Jun Bae Lee, Yongin-si (KR); Chun Ho Park, Yongin-si (KR); Moung Seok Yoon, Daejeon (KR); Hee Chang Ryoo, Seoul (KR); Seon Mi Kim, Seongnam-si (KR)

(73) Assignee: COSMAX CO., LTD., Gyeonggi-Do (KR)

( * ) Notice: Subject to any disclaimer, the term of this patent is extended or adjusted under 35 U.S.C. 154(b) by 290 days.

(21) Appl. No.: 15/024,382

(22) PCT Filed: Sep. 27, 2013

(86) PCT No.: PCT/KR2013/008704
§ 371 (c)(1),
(2) Date: Mar. 24, 2016

(87) PCT Pub. No.: WO2015/046648
PCT Pub. Date: Apr. 2, 2015

(65) Prior Publication Data
US 2016/0213579 A1 Jul. 28, 2016

(30) Foreign Application Priority Data
Sep. 26, 2013 (KR) .................. 10-2013-0114540

(51) Int. Cl.
*A61Q 19/00* (2006.01)
*A61K 8/02* (2006.01)
(Continued)

(52) U.S. Cl.
CPC .............. *A61K 8/0295* (2013.01); *A61K 8/03* (2013.01); *A61K 8/06* (2013.01); *A61K 8/342* (2013.01);
(Continued)

(58) Field of Classification Search
None
See application file for complete search history.

(56) References Cited

U.S. PATENT DOCUMENTS 6,325,995 B1 * 12/2001 El-Nokaly et al. ...... A61K 7/00
424/64
2008/0103207 A1 5/2008 Dayan

FOREIGN PATENT DOCUMENTS

KR 100452757 10/2004
KR 100525842 10/2005
(Continued)

OTHER PUBLICATIONS

KR20130030093A paragraph 70 translation 2013, 1 page. (Year: 2013).*

(Continued)

*Primary Examiner* — Ernst V Arnold
(74) *Attorney, Agent, or Firm* — Cantor Colburn LLP (57) ABSTRACT

A method for preparing a liquid crystal emulsion includes: a) mixing, warming and dissolving intercellular lipid ingredients, non-polyoxyethylene (POE) based non-ionic surfactant, higher fatty alcohol, oil and wax to provide an oil phase part; b) mixing, warming and dissolving water, polyol and the other aqueous phase ingredients to provide an aqueous phase part; c) adding the oil phase part to the aqueous phase part, followed by agitation; d) introducing a viscosity modifier to the mixture solution under agitation; e) subjecting the mixture solution to rapid cooling under vacuum while carrying out debubbling under vacuum; and f) filtering the
(Continued)

mixture solution through a filtering paper or filtering cloth. Provided is a stable liquid crystal emulsion having a multilayer lamellar structure including a large amount of intercellular lipid ingredients through a process using rapid cooling. The liquid crystal emulsion has an oil phase part and an aqueous phase part.

6 Claims, 4 Drawing Sheets

(51) Int. Cl.
| | | |
|---|---|---|
| *A61K 8/92* | (2006.01) | |
| *A61K 8/34* | (2006.01) | |
| *A61K 8/03* | (2006.01) | |
| *A61K 8/06* | (2006.01) | |
| *A61K 8/36* | (2006.01) | |
| *A61K 8/37* | (2006.01) | |
| *A61K 8/41* | (2006.01) | |
| *A61K 8/55* | (2006.01) | |
| *A61K 8/58* | (2006.01) | |
| *A61K 8/60* | (2006.01) | |
| *A61K 8/63* | (2006.01) | |
| *A61K 8/68* | (2006.01) | |
| *A61K 8/891* | (2006.01) | |

(52) U.S. Cl.
CPC .............. *A61K 8/345* (2013.01); *A61K 8/361* (2013.01); *A61K 8/37* (2013.01); *A61K 8/41* (2013.01); *A61K 8/553* (2013.01); *A61K 8/585* (2013.01); *A61K 8/60* (2013.01); *A61K 8/602* (2013.01); *A61K 8/63* (2013.01); *A61K 8/68* (2013.01); *A61K 8/891* (2013.01); *A61K 8/92* (2013.01); *A61K 8/922* (2013.01); *A61Q 19/00* (2013.01); *A61K 2800/80* (2013.01)

(56) References Cited

FOREIGN PATENT DOCUMENTS

| KR | 100588743 | 6/2006 |
|---|---|---|
| KR | 100830153 | 5/2008 |
| KR | 100867679 | 11/2008 |
| KR | 20100011213 | 2/2010 |
| KR | 20110057819 | 6/2011 |
| KR | 20120044067 | 5/2012 |
| KR | 20130030093 | 3/2013 |

OTHER PUBLICATIONS

DERWENT-ACC-NO:2003-565436 of KR2002076874 2002; Abstract 2 pages. (Year: 2002).*
Written Opinion of the International Searching Authority Translation PCT/KR2013008704 dated Sep. 2013; 9 pages. (Year: 2013).*
Eccleston, Multiple-phase oil-in-water emulsions, Journal of the Society of Cosmetic Chemists 41, 1990, pp. 1-22.
Elias, et al., Mammalian Epidermal Barrier Layer Lipids: Composition and Influence on Structure, The Journal of Investigative Dermatology vol. 69 No. 6, 1977, pp. 535-546.
Guo, et al., Simulation Study of the Structure and Phase Behavior of Ceramide Bilayers and the ROle of Lipid Headgroup Chemistry, Journal of Chemical Theory and Computation, 2013, pp. 5116-5126.
McClements, et al., Oil exchange between oil-in-water emulsion droplets stabilised with a non-ionic surfactant, Food Hydrocolloids vol. 6 No. 5, 1992, pp. 415-422.
Wertz, The nature of the epidermal barrier: biochemical aspects, Advanced Drug Delivery Reviews 18, 1996, pp. 283-294.
International Search Report—PCT/KR2013/008704 dated Jun. 27, 2014.

* cited by examiner

METHOD FOR PREPARING MULTILAYER LAMELLAR LIQUID CRYSTAL EMULSION INCLUDING INTERCELLULAR LIPIDS

TECHNICAL FIELD

The present disclosure relates to a method for preparing a multilayer lamellar liquid crystal emulsion including intercellular lipids. More particularly, the present disclosure relates to a method for preparing a stable liquid crystal emulsion having a multilayer lamellar structure including intercellular lipids through a process using rapid cooling, wherein the liquid crystal emulsion has an oil phase part that contains intercellular lipid ingredients, non-polyoxyethylene (POE) based non-ionic surfactant, higher fatty alcohol, oil and wax, and an aqueous phase part that contains water, polyol and the other aqueous phase ingredients.

BACKGROUND ART

The stratum corneum that is the outermost layer of the human skin functions to protect the skin from external harmful environment and harmful materials and interrupts evaporation of the moisture in the human body, thereby functioning as a skin barrier preventing skin dryness. Lipid ingredients play a particularly important role in the stratum corneum. Elias and coworkers have reported that the lamellar structure formed of the lipid ingredients in the stratum corneum is the origin of such a skin barrier function (J. Invest. Dermatol. 69: 535-546, 1977). In addition, although there is a difference depending on the experimental method and the position of a skin tissue, Wertz and coworkers have reported that intercellular lipids substantially include about 50% of ceramides, 20-25% of cholesterol, 20-25% of free fatty acids, about 10% of cholesterol ester, 1-2% of cholesterol sulfate, a small amount of phospholipid, a small amount of phytosphingosine and a small amount of triglycerides (Adv. Drug. Deliv. Rev. 18: 283-294, 1996).

Intercellular lipid ingredients, particularly ceramides and cholesterol, are mostly hydrophobic, highly crystallizable and sparingly soluble materials. They are not dissolved completely into an oil phase that is a dispersion phase in a general oil-in-water emulsion formulation but are partially present in an aqueous phase that is a continuous phase. For this reason, problems related with formulation stability, such as gelation, may occur.

To solve the above-mentioned problem, there has been suggested a stabilization method including forming granules (particles) including intercellular lipids and other ingredients and adding the granules in the last step during the preparation of an emulsion (Korean Patent Application No. 2008-0072335). However, the method is problematic in that the amount of intercellular lipids that may be used actually in a skin application agent is decreased due to an excessive amount of encapsulating base used for an encapsulation step, and an encapsulating agent based on saccharides or polymers causes degradation of the feeling of use of a skin application agent.

As a part of attempts to stabilize intercellular lipids in emulsion, there has been suggested a method including preliminarily forming a liquid crystal base and adding it in the last step during the preparation of a general oil-in-water emulsion (Korean Patent Publication Nos. 10-0452757, 10-0525842, 10-0830153, 10-0867679). However, such a liquid crystal base is present mostly in a wax or paste phase having high hardness at room temperature, and thus shows low compatibility during processing. In addition, the preparation of such a liquid crystal base requires use of an excessive amount of lecithin and higher fatty alcohol. However, such materials undesirably have a stiff feeling of use. Moreover, when using a liquid crystal base, emulsion undergoes an increase in viscosity or hardness with time. It is thought that this is because the surfactant micelles present in the emulsion attack the oil particles of the liquid crystal emulsion obtained from the liquid crystal base, resulting in degradation of the stability of liquid crystal emulsion. Similarly, there has been reported that surfactant particles present in the form of micelles cause mass transfer among the oil particles of oil-in-water emulsion (Food Hydrocolloids, 6(5): 415-422, 1992).

Finally, there has been an attempt to form a liquid crystal emulsion through a direct emulsification process in order to stabilize intercellular lipids in emulsion. Korean Patent Publication No. 10-0588743 discloses a method for preparing a liquid crystal emulsion having a multilayer lamellar structure including a POE-based surfactant, intercellular lipids, higher fatty alcohol, or the like. However, such a liquid crystal emulsion including a POE-based surfactant causes swelling in an emulsion system, thereby affecting the overall stability of an emulsion system (G. M. Eccleston, Miltiple-phase oil-in-water emulsions, J. Soc. Cosmet. Chem., (41) 1-22, 1990). In addition, according to the above document, a phase transition emulsification process using temperature control is applied. In general, a phase transition emulsification process is advantageous in that it produces particles having a uniform size. However, such a process is complicated and requires use of a slow cooling step in a natural cooling mode, and thus has low time efficiency. According to Korean Patent Application No. 2011-0093634, a liquid crystal emulsion is prepared by using a glucoside surfactant, ceramide and oil. However, in this case, a slow cooling mode is applied. According to the above document, it is said that slow cooling provides liquid crystal particles having an adequate size, as compared to rapid cooling that produces very small particles having a low product value. However, according to the study of the inventors of the present disclosure, controlling a particle size depends on a compositional ratio of contents rather than a cooling mode. In addition, another patent document (Korean Patent Publication No. 10-0830153) that belongs to the same category discloses that cetostearyl alcohol, a higher fatty alcohol, present in an oil phase moves toward the interface of particles, while it precipitates in the form of crystals through a cooling step, in a process of forming liquid crystals, and application of rapid cooling at that time prevents cetostearyl alcohol from moving toward the interface and causes it to be present in oil in an oversaturated sate, resulting in a decrease in liquid crystal formation and a drop in viscosity. However, a process of forming liquid crystals does not include precipitation of a higher fatty alcohol that has been dissolved in an oil phase in the form of crystals at high temperature through a cooling step, but includes phase transition of a higher fatty alcohol into a liquid crystal phase having both of solid properties and liquid properties and orientation thereof at the particle interface in a certain direction together with the surfactant. In addition, although the above document discloses that rapid cooling prevents cetostearyl alcohol from moving toward the interface, cetostearyl alcohol itself is an amphiphilic material, and thus is not present in an oil phase but tends to move toward the interface. Therefore, the moving rate of cetostearyl alcohol to the interface may be controlled by the type of oil used in forming liquid crystals and cooling rate. Further, the above document discloses that cetostearyl alcohol is present in an amount equal to or higher than its solubility in oil. However, incorporation of an excessive amount of cetostearyl alcohol may cause precipitation of a higher fatty alcohol and degradation of a feeling of use.

Under these circumstances, the present inventors have conducted active studies to overcome the above-mentioned problems. After the studies, we have found that it is possible to prepare a stable liquid crystal emulsion having a multilayer lamellar structure including a large amount of intercellular ingredients through a rapid cooling process, wherein the liquid crystal emulsion has an oil phase part that contains intercellular lipid ingredients, non-POE based non-ionic surfactant, higher fatty alcohol, oil and wax, and an aqueous phase part that contains water, polyol and the other aqueous phase ingredients. The present disclosure is based on this finding.

DISCLOSURE

Technical Problem

A technical problem to be solved by the present disclosure is to provide a method for preparing a stable liquid crystal emulsion having a multilayer lamellar structure including a large amount of intercellular ingredients through a rapid cooling process, wherein the liquid crystal emulsion has an oil phase part that contains intercellular lipid ingredients, non-POE based non-ionic surfactant, higher fatty alcohol, oil and wax, and an aqueous phase part that contains water, polyol and the other aqueous phase ingredients.

Another technical problem to be solved by the present disclosure is to provide a cosmetic composition including the liquid crystal emulsion obtained by the above-mentioned method for preparing a multilayer lamellar liquid crystal emulsion including intercellular lipids.

Technical Solution

In one general aspect, there is provided a method for preparing a liquid crystal emulsion, including the steps of:

a) mixing, warming and dissolving intercellular lipid ingredients, non-polyoxyethylene (POE) based non-ionic surfactant, higher fatty alcohol, oil and wax to provide an oil phase part;

b) mixing, warming and dissolving water, polyol and the other aqueous phase ingredients to provide an aqueous phase part;

c) adding the oil phase part to the aqueous phase part, followed by agitation;

d) introducing a viscosity modifier to the mixture solution under agitation;

e) subjecting the mixture solution to rapid cooling while carrying out debubbling under vacuum; and f) filtering the mixture solution through a filtering paper or filtering cloth.

According to an embodiment, the oil of the oil phase part in step a) may be at least one selected from the group consisting of polar oil such as ester oil and triglyceride oil, nonpolar oil such as hydrocarbon oil and mineral oil, vegetable oil and silicon oil.

According to another embodiment, the wax may be at least one selected from the group consisting of higher fatty alcohols, fatty acids, vegetable wax, mineral wax, synthetic wax, ozokerite, cetyl palmitate, sorbitan palmitate, bees wax, lipids and lipid peptides.

According to still another embodiment, the other aqueous phase ingredients of the aqueous phase part in step b) may further include a water-soluble active ingredient. The water-soluble active ingredient may include any material that can be dissolved in water to form an aqueous phase part and particular examples thereof include a material having an anti-wrinkle function, a whitening material and natural extract.

The anti-wrinkle material may include adenosine, and the whitening material my include albutin, niacin amide, or the like. In addition, the natural extract may include natural vegetable, animal or mineral extract extracted from aloe, green tea, citrus, gingko leaves, or the like. The water-soluble active ingredient is not limited to the above-mentioned examples.

Figure 1:
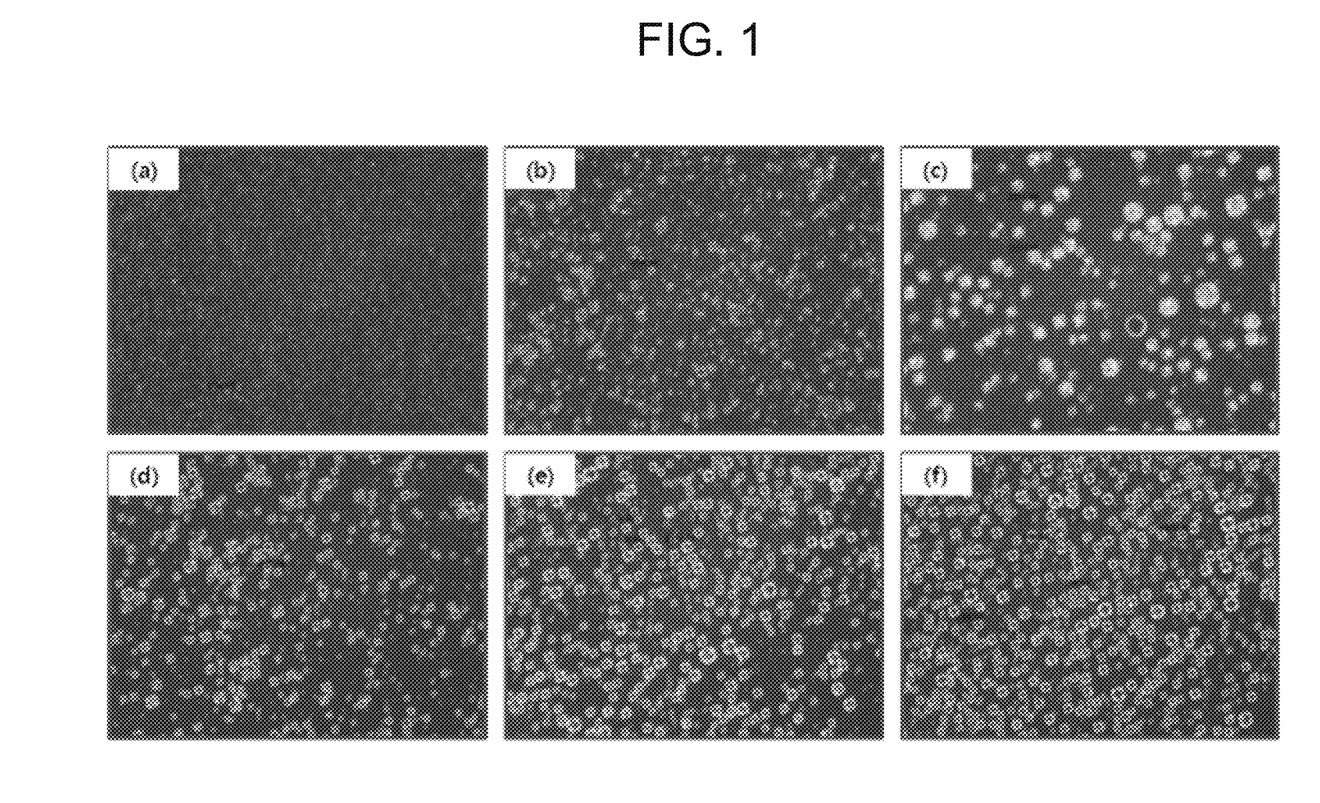
FIG. 1 is an image of the liquid crystal emulsion according to an embodiment observed by a polarization microscope at different temperatures, wherein the Maltose cross pattern unique to a multilayer lamellar structure can be observed by a polarization microscope starting from about 45° C. (a: 73° C., b: 63° C., c: 53° C., d: 45° C., e: 35° C., f: 25° C.).

In the method according to the present disclosure, the oil phase part (inner phase, dispersion phase) and aqueous phase part (outer phase, continuous phase) are agitated at 70° C. or higher in step c), and then the size and state of particles are observed right after the agitation. After the observation, it can be seen that emulsion having a particle size of about 1-2 μm is formed as shown in (a) of FIG. 1. Step d) is carried out to modify the viscosity of an emulsion and to rapidly reducing the temperature of the mixture solution. By virtue of the use of a viscosity modifier in step d), the temperature is reduced from 70° C. or higher to about 60-70° C. During this step, the particle size is grown to 3-10 μm as shown in (b) of FIG. 1.

In the method according to the present disclosure, step e) is a cooling step using a rapid cooling mode. The higher fatty alcohols that have been dissolved in the oil phase undergo a transition from a liquid phase to a liquid crystal phase through the rapid cooling process, while they move toward the interface. Then, the higher fatty alcohols that have undergone a transition to a liquid crystal phase are oriented in a certain direction at around the interface together with the surfactant and intercellular lipid ingredients having amphiphilic properties, thereby forming a multilayer lamellar structure. While the liquid crystal emulsion undergoes a rapid cooling process, it forms a stable liquid crystal emulsion having a multilayer lamellar structure, as shown in (f) of FIG. 1.

Figure 2:
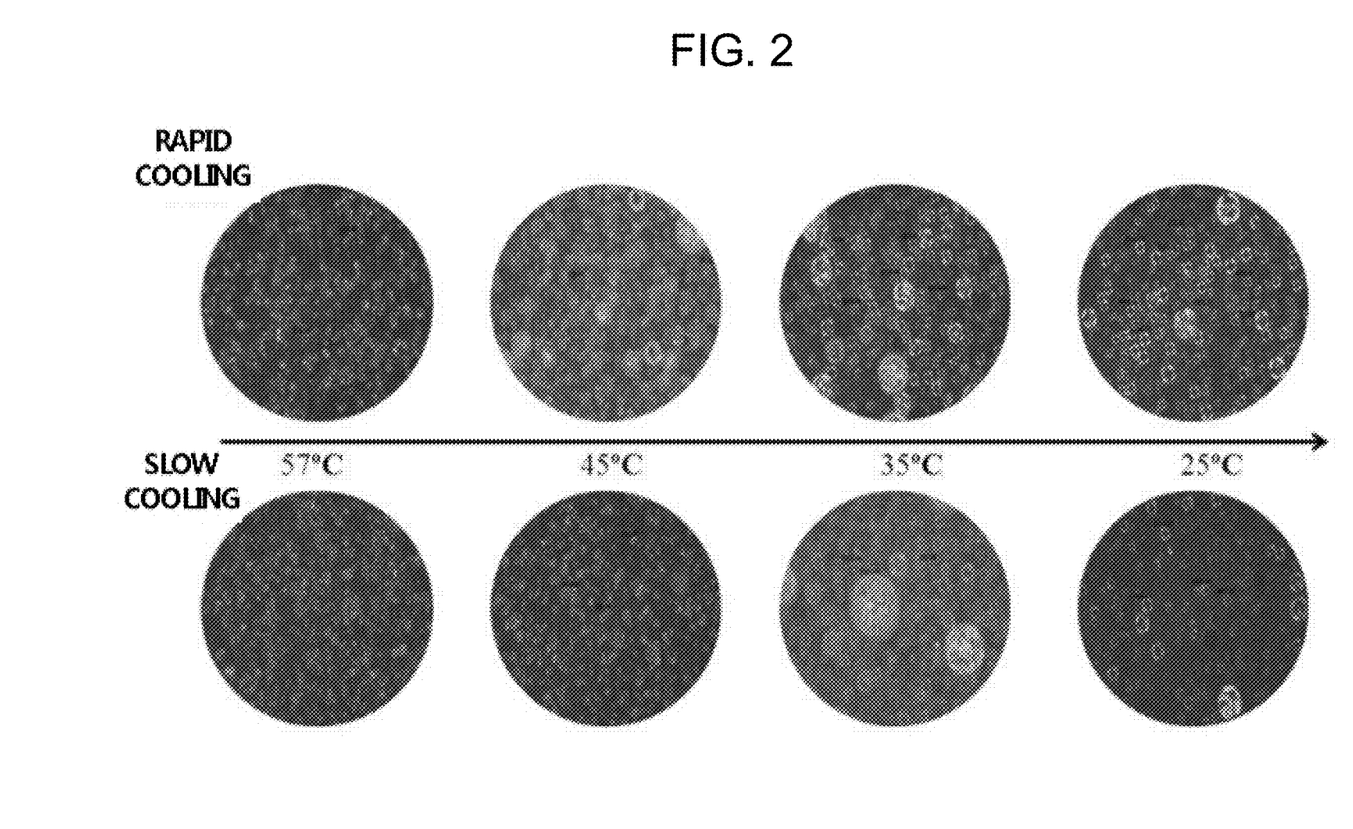
FIG. 2 is an image illustrating a difference in particles as a function of cooling rate of liquid crystal emulsion, as taken by a polarization microscope.

According to some embodiments, in the case of the rapid cooling process as shown in FIG. 2, the higher fatty alcohols undergo a transition from a liquid phase to a liquid crystal phase at about 40-45° C. and are oriented well at the interface to form liquid crystal emulsion particles having a size of 5-15 μm. On the contrary, in the case of slow cooling, the liquid crystal array is destroyed while the higher fatty alcohols undergo a transition from an oil phase (dispersion phase) to an aqueous phase (continuous phase), resulting in a decrease in number of liquid crystal particles forming a multilayer lamellar structure and a drop in density of a lamellar structure as compared to the rapid cooling process. Therefore, it can be seen that a rapid cooling process according to the present disclosure forms a more stable multilayer lamellar structure as compared to a slow cooling process (FIG. 2).

In the method according to the present disclosure, step f) is for filtering the liquid crystal emulsion obtained from the preceding step through a filtering cloth.

In the method according to the present disclosure, the liquid crystal emulsion is obtained in-situ by the process for preparing an emulsion, not by post-addition of a preliminarily formed liquid crystal base to an emulsion.

In a general oil-in-water emulsion formulation, intercellular lipid ingredients, particularly ceramides and cholesterol, most of which are hydrophobic, highly crystallizable and sparingly soluble materials, are not dissolved in an oil phase (dispersion phase) completely, but are partially present in an aqueous phase (continuous phase). Due to this, some problems related with formulation stability, such as gelation, may occur.

To solve the above-mentioned problems and to stabilize intercellular lipids in emulsion, a liquid crystal emulsion may be obtained by a method that includes preliminarily forming a liquid crystal base and adding it in the last step of a process for preparing an oil-in-water emulsion, or forming a liquid crystal emulsion through a direct emulsification process in which a slow cooling step using a natural cooling mode is applied.

However, such a method including post-addition of a liquid crystal base shows low compatibility due to the high hardness of a liquid crystal base at room temperature. In addition, use of a liquid crystal base undesirably causes an increase in viscosity or hardness of emulsion with time. Meanwhile, the method for preparing a liquid crystal emulsion through a direct emulsification process uses a polyoxyethylene (POE)-based surfactant. Such a liquid crystal emulsion including a POE-based surfactant causes swelling in the emulsion system, thereby affecting the overall stability of the emulsion system. In the swelled emulsion system, various intercellular lipids and higher fatty alcohols oriented toward the inner part while the interface is destroyed are come out to the aqueous phase (continuous phase), thereby causing an increase in viscosity and hardness with time and degradation of the overall stability of emulsion. Furthermore, when preparing a liquid crystal base by using a slow cooling step, an undesirably long time is required for preparing a liquid crystal emulsion. Thus, the above-mentioned methods are not preferred.

Therefore, the method for preparing a liquid crystal emulsion having a multilayer lamellar structure including intercellular lipids according to the present disclosure does not use post-addition of a liquid crystal base, but uses a non-POE based non-ionic surfactant and a rapid cooling step. In this manner, it is possible to obtain an oil-in-water liquid crystal emulsion having a stable multilayer lamellar structure including intercellular lipids. The present disclosure is based on this.

According to some embodiments, the stability of intercellular lipid ingredients is determined in a conventional emulsion (Comparative Example 5) and a liquid crystal emulsion (Example 1). In the case of the liquid crystal emulsion (Example 1), it forms a multilayer lamellar structure, and thus amphiphilic intercellular lipid ingredients are present stably in the lamellar structure and it shows a small difference in viscosity. Meanwhile, in the case of a conventional emulsion (Comparative Example 5), it causes a decrease in moving rate of intercellular lipid ingredients from the inner phase to the outer phase in the emulsion under refrigeration and cooling conditions, and thus shows a smaller increase in viscosity as compared to room temperature and high temperature conditions. However, the conventional emulsion causes an increase in viscosity by at least three times as compared to the liquid crystal emulsion (Example 1). In addition, in the conventional emulsion under room temperature and high temperature conditions, intercellular lipid ingredients that have been present in the inner phase right after the preparation move toward the outer phase through the interface, and then undergo a gelation process, resulting in a rapid increase in viscosity to a non-detectable extent. As a result, it can be seen that the liquid crystal emulsion according to the present disclosure provides a stable liquid crystal emulsion having a multilayer lamellar structure including intercellular lipid ingredients at various temperature conditions (Test Example 4).

In the present disclosure, intercellular lipids may be any known intercellular lipid ingredients, and particular examples thereof include ceramides, cholesterol, triglycerides, phytosphingosine and free acids.

In the present disclosure, ceramide may be at least one selected from the group consisting of natural ceramides and pseudo ceramides. Natural ceramides are those present in the nature and include ceramide-1, ceramide-2, ceramide-3, ceramide-4, ceramide-5, ceramide-5, ceramide-6, ceramide-6, ceramide-7, ceramide-8, or the like.

In the present disclosure, the non-ionic surfactant may be any non-ionic surfactant known to those skilled in the art. Particularly, the non-ionic surfactant may be at least one selected from the group consisting of lecithin, sorbitan-based surfactants and glucoside-based surfactants.

In the present disclosure, the non-ionic surfactant may be a combination of lecithin, a sorbitan-based surfactant and a glucoside-based surfactant.

According to the present disclosure, the surfactant is not a POE-based non-ionic surfactant. As described above, use of a POE-based non-ionic surfactant may cause swelling of liquid crystal emulsion particles, thereby adversely affecting emulsion stability.

According to the following test examples, a mixture of lecithin, a sorbitan-based surfactant and a glucoside-based surfactant is used as surfactant. When using each of the above-mentioned surfactants alone, as shown in (a) of FIG. 3, lecithin causes the problems of liquid crystal stability and stiff feeling of use. In addition, as shown in (b) of FIG. 3, the sorbitan-based surfactant provides an excessively large particle size, resulting in degradation of formulation stability. As shown in (c) of FIG. 3, the glucoside-based surfactant provides relatively small liquid crystal particles and cannot form liquid crystals having desired quality. On the contrary, when mixing the three types of surfactants, it is possible to obtain a liquid crystal emulsion having a uniform particle size and desired quality and to improve liquid crystal stability, as shown in (d) of FIG. 3. As a result, it can be seen that use of a combination of the three types of surfactants rather than use of a single type of surfactant is favorable to preparation of a stable liquid crystal emulsion (Test Example 1 and FIG. 3).

In the present disclosure, lecithin is used in an amount of 0.05-1 wt %, the sorbitan-based surfactant is used in an amount of 0.1-5 wt %, and the glucoside-based surfactant is used in an amount of 0.1-5 wt %, based on the total weight of emulsion.

When each surfactant is used in an amount less than the above-defined range, excessively large liquid crystal emulsion particles may be formed or emulsification itself cannot be accomplished. In addition, when each surfactant is used in an amount larger than the above-defined range, excessively small emulsion particles may be formed, and thus it is not possible to realize properties as liquid crystals.

In the present disclosure, the polyol may be at least one selected from the group consisting of propylene glycol, dipropylene glycol, 1,3-butylene glycol, pentylene glycol, 1,2-octanediol and 1,2-hexanediol, and may be used in an amount of 1-30 wt % based on the total weight of emulsion.

In the present disclosure, the rapid cooling is carried out from 70° C.-90° C. to 40° C.-50° C. within 5-15 minutes. This is because the temperature of transition of higher fatty alcohol to a liquid crystal phase is known to be 40° C.-50° C.

According to the following test examples, the liquid crystal emulsion (Example 1) obtained through a rapid cooling process shows a stable multilayer lamellar structure for 3 months at the all tested temperature conditions. On the contrary, the liquid crystal emulsion (Comparative Example 4) obtained through a slow cooling process causes degradation or collapse of its liquid crystal state after 3 months at room temperature, 37° C., 45° C. and under CYC thermostat storage condition, thereby causing the problem of an increase in viscosity (Test Example 3).

In the present disclosure, the liquid crystal emulsion has a multilayer lamellar structure.

Figure 4:
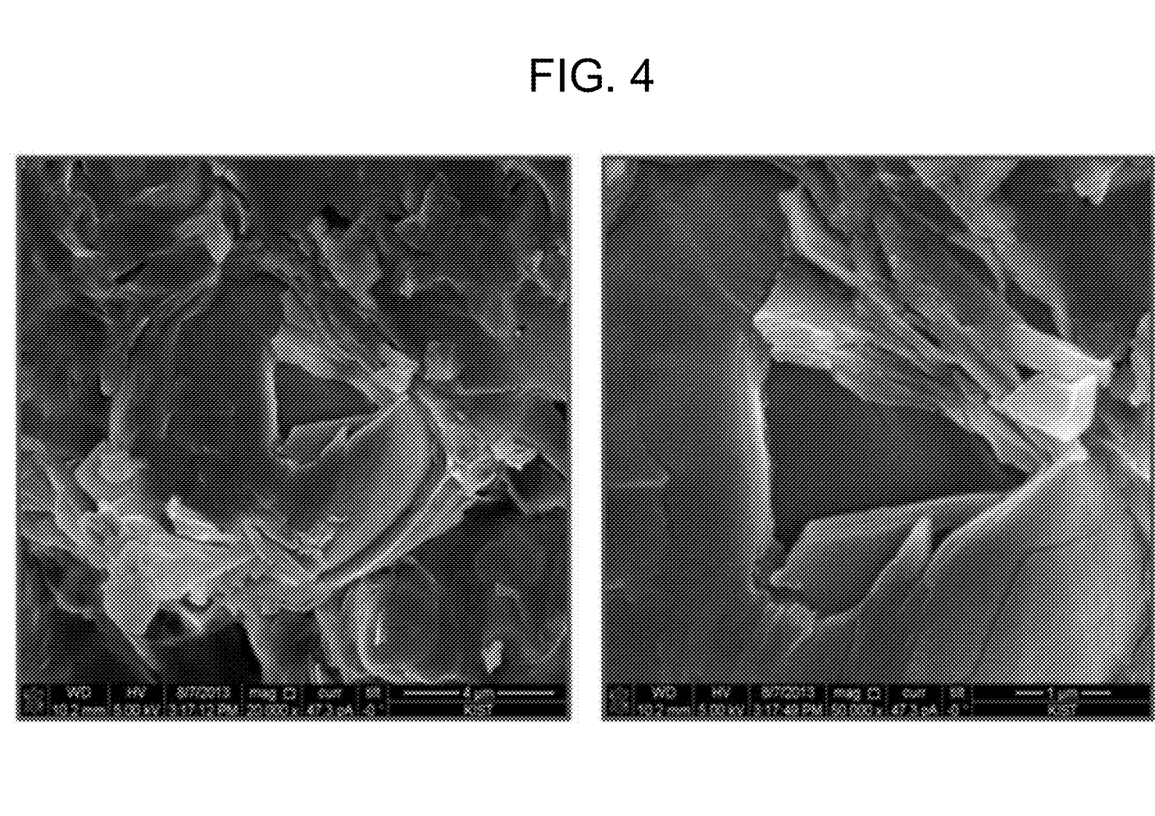
FIG. 4 is an electron microscopic image illustrating the multilayer lamellar structure of the liquid crystal emulsion according to the present disclosure (left: liquid crystal emulsion having a multilayer lamellar structure, right: magnified view of a multilayer lamellar structure).

As shown in FIG. 4, the liquid crystal emulsion according to the present disclosure has a multilayer lamellar structure when observed by an electron microscope.

In another aspect, there is provided a cosmetic composition including the liquid crystal emulsion obtained by the above-described method.

According to the following test examples, after carrying out a skin safety test by using the liquid crystal emulsion of Example 1, the liquid crystal emulsion causes skin irritation with a level less than 1, suggesting that it causes no irritation. As a result, it can be seen that the cosmetic composition including the liquid crystal emulsion obtained by the method according to the present disclosure is safe when applied to the skin (Test Example 5).

In the present disclosure, the composition may have a formulation selected from the group consisting of a solution, suspension, emulsion, paste, gel, cream, lotion, powder, soap, oil, powdery foundation, emulsified foundation, wax-like foundation and spray.

Advantageous Effects

According to the embodiments of the present disclosure, there is provided a stable liquid crystal emulsion having a multilayer lamellar structure including intercellular lipids. In the conventional oil-in-water emulsion, it is difficult to stabilize intercellular lipid ingredients. However, in the liquid crystal emulsion according to the present disclosure, intercellular lipid ingredients are oriented regularly, thereby improving stability in the formulation.

BEST MODE

Exemplary embodiments now will be described more fully hereinafter with reference to the accompanying drawings, in which exemplary embodiments are shown. This disclosure may, however, be embodied in many different forms and should not be construed as limited to the exemplary embodiments set forth therein.

Test Example 1: Test for Determining Stability Depending on Surfactant

TABLE 1

| | Ingredients | Comp. Ex. 1 | Comp. Ex. 2 | Comp. Ex. 3 | Ex. 1 |
|---|---|---|---|---|---|
| 1. | Vegetable wax | 0.5 | 0.5 | 0.5 | 0.5 |
| 2. | Cetostearyl alcohol | 2.0 | 2.0 | 2.0 | 2.0 |
| 3. | Cholesterol | 0.5 | 0.5 | 0.5 | 0.5 |
| 4. | Ceramide-3 | 0.5 | 0.5 | 0.5 | 0.5 |
| 5. | Stearic acid | 1.0 | 1.0 | 1.0 | 1.0 |
| 6. | Phytosphingosine | 0.3 | 0.3 | 0.3 | 0.3 |
| 7. | Behenyl alcohol | 0.5 | 0.5 | 0.5 | 0.5 |
| 8. | Lecithin | 0.2 | — | — | 0.2 |
| 9. | Sorbitan Palmitate | — | 1 | — | 1 |
| 10. | C12-20Alkyl Glucoside | — | — | 1 | 1 |
| 11. | Caprylic/capric triglyceride | 10.0 | 10.0 | 10.0 | 10.0 |
| 12. | Dimethicone | 2.0 | 2.0 | 2.0 | 2.0 |
| 13. | Cyclopentasiloxane | 2.0 | 2.0 | 2.0 | 2.0 |
| 14. | D.I. Water | To 100 | To 100 | To 100 | To 100 |
| 15. | EDTA-2Na | 2.0 | 2.0 | 2.0 | 2.0 |
| 16. | Glycerin | 7.0 | 7.0 | 7.0 | 7.0 |
| 17. | Butylene Glycol | 5.0 | 5.0 | 5.0 | 5.0 |
| 18. | 1% Carbomer solution | 15 | 15 | 15 | 15 |
| 19. | Triethanolamine | 0.12 | 0.12 | 0.12 | 0.12 |
| 20. | Preservatives | qsad | qsad | qsad | qsad |
| 21. | Perfume | 0.1 | 0.1 | 0.1 | 0.1 |

<Preparation Method>

1) In Table 1, ingredients 3-6 are intercellular lipids, 8-10 are non-POE based non-ionic surfactants, 2 and 7 are higher fatty alcohols, 11-13 are oil, 1 is wax, 14-17 are water-soluble ingredients, wherein 16 and 17 are polyols, 18 and 19 are viscosity modifiers, 20 is a preservative, and 21 is a perfume ingredient.

2) In Table 1, ingredients 1-13 are mixed and dissolved at 70-80° C. to provide an oil phase solution.

3) In a separate container, ingredients 14-17 of Table 1 are mixed, and then warmed and dissolved to 70-80° C. to provide an aqueous phase solution.

4) The oil phase solution of 2) is added to the aqueous phase solution of 3), followed by agitation with a homo-mixer.

5) Then, ingredient 18 of Table 1 is mixed with the mixture solution obtained from 4), followed by mixing with ingredient 19.

6) Right after carrying out the process of 5), the reaction mixture is subjected to rapid cooling so that it is cooled to 40° C. within 10 minutes. Then, ingredients 20 and 21 of Table 1 are introduced and the reaction mixture is debubbled.

Figure 3:
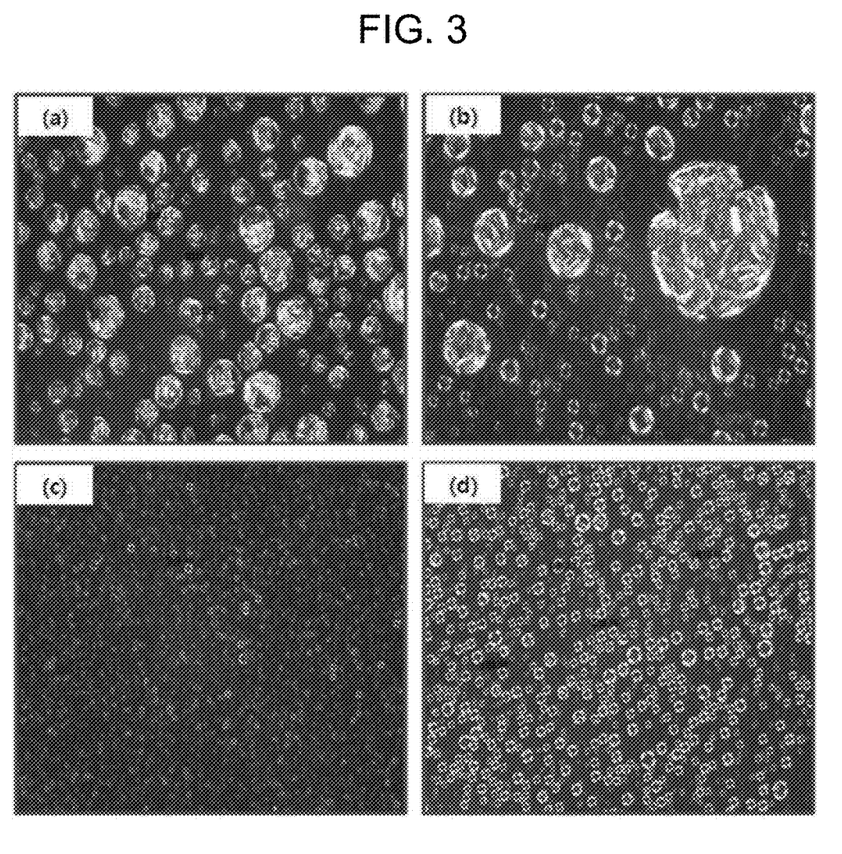
FIG. 3 is an image illustrating liquid crystal emulsions obtained by using different types of surfactants, as taken by a polarization microscope (a: lecithin, b: sorbitan-based surfactant, c: glucoside-based surfactant, d: combination of surfactants a)-c)).

Comparative Examples 1-3 and Example 1 obtained according to Table 1 are observed with a polarization microscope. As shown in FIG. 3, use of a combination of surfactants ((d) of FIG. 3) improves the stability of liquid crystals much more than use of a single surfactant alone ((a), (b), (c) of FIG. 3).

Test Example 2: Preparation of Comparative Examples and Example

TABLE 2

| | Ingredients | Amount (%) |
|---|---|---|
| 1. | Vegetable wax | 0.5 |
| 2. | Cetostearyl alcohol | 2.0 |
| 3. | Cholesterol | 0.5 |
| 4. | Ceramide-3 | 0.5 |
| 5. | Stearic acid | 1.0 |
| 6. | Phytosphingosine | 0.3 |
| 7. | Behenyl alcohol | 0.5 |
| 8. | Lecithin | 0.2 |
| 9. | Sorbitan Palmitate | 1 |
| 10. | C12-20Alkyl Glucoside | 1 |
| 11. | Caprylic/capric triglyceride | 10.0 |
| 12. | Dimethicone | 2.0 |
| 13. | Cyclopentasiloxane | 2.0 |
| 14. | D.I. Water | To 100 |
| 15. | EDTA-2Na | 2.0 |
| 16. | Glycerin | 7.0 |
| 17. | Butylene Glycol | 5.0 |
| 18. | 1% Carbomer solution | 15 |
| 19. | Triethanolamine | 0.12 |
| 20. | Preservatives | qsad |
| 21. | Perfume | 0.1 |

<Preparation Method>

1) In Table 2, ingredients 3-6 are intercellular lipids, 8-10 are non-POE based non-ionic surfactants, 2 and 7 are higher fatty alcohols, 11-13 are oil, 1 is wax, 14-17 are water-soluble ingredients, wherein 16 and 17 are polyols, 18 and 19 are viscosity modifiers, 20 is a preservative, and 21 is a perfume ingredient.

2) In Table 2, ingredients 1-13 are mixed and dissolved at 70-80° C. to provide an oil phase solution.

3) In a separate container, ingredients 14-17 of Table 2 are mixed, and then warmed and dissolved to 70-80° C. to provide an aqueous phase solution.

4) The oil phase solution of 2) is added to the aqueous phase solution of 3), followed by agitation with a homo-mixer.

5) Then, ingredient 18 of Table 2 is mixed with the mixture solution obtained from 4), followed by mixing with ingredient 19 of Table 2.

6) In Example 1, right after carrying out the process of 5), the reaction mixture is subjected to rapid cooling so that it is cooled to 40° C. within 10 minutes. Then, ingredients 20 and 21 of Table 2 are introduced and the reaction mixture is debubbled (Example 1 in Test Example 2 is the same as Example 1 in Test Example 1).

7) In Comparative Example 4, after carrying out the process of 5), the reaction mixture is allowed to stand at room temperature and then ingredients 20 and 21 of Table 2 are introduced thereto, followed by debubbling.

Example 1 and Comparative Example 4 obtained according to Table 2 are observed with a polarization microscope. As shown in FIG. 2, a rapid cooling process provides a liquid crystal emulsion having higher stability as compared to a slow cooling process.

Test Example 3: Test for Determining Stability of Liquid Crystal Emulsion Particles Depending on Cooling Rate Example 1 and Comparative Example 4 are observed for the state of liquid crystal emulsion particles depending on temperature by using a polarization microscope. In this manner, the particle size, density and stability of the liquid crystal emulsion according to each of Example 1 and Comparative Example 4 are determined.

After the observation, as shown in FIG. 2, a rapid cooling process allows higher fatty alcohols to undergo a transition from a liquid phase to a liquid crystal phase at about 40-45° C. while they are oriented well at the interface, thereby forming liquid crystal emulsion particles having a size of 5-15 μm. On the contrary, a slow cooling process causes higher fatty alcohols to move from an oil phase (dispersion phase) to an aqueous phase (continuous phase), resulting in collapse of liquid crystal array. Thus, as shown in FIG. 2, it can be seen that the number of liquid crystal emulsion particles forming a multilayer lamellar structure is small and the density of multilayer lamellar structure is lower as compared to a rapid cooling process.

In addition, to determine stability of a liquid crystal emulsion in Example 1 and Comparative Example 4 depending on temperature, each composition is tested for its stability under the conditions of refrigeration (−18° C.), cooling (4° C.), room temperature, 37° C., 45° C. and in a CYC (12 hours for each of the conditions of refrigeration, room temperature and 45° C.) thermostat for 3 months. The results are shown in the following Table 3.

TABLE 3

| | Refrigeration (−18° C.) | Cooling (4° C.) | Room Temperature | 37° C. | 45° C. | CYC |
|---|---|---|---|---|---|---|
| Ex. 1 | Stable | Stable | Stable | Stable | Stable | Stable |
| Comp. Ex. 4 | Stable | Stable | Unstable | Unstable | Liquid crystal weakened | Unstable |

As shown in FIG. 3, the liquid crystal emulsion (Example 1) obtained through a rapid cooling process shows a stable multilayer lamellar structure for 3 months under all temperature conditions. However, it is shown that the liquid crystal emulsion (Comparative Example 4) obtained through a slow cooling process causes weakening of liquid crystals or collapse of liquid crystals and an increase in viscosity under the storage conditions of room temperature, 37° C., 45° C. and under a thermoset storage condition.

Test Example 4: Test for Stability of Intercellular Lipid Ingredients in Formulation To determine the stability of intercellular lipid ingredients in a formulation, a conventional emulsion and a liquid crystal emulsion are prepared. The conventional emulsion is prepared by excluding ingredients 1 and 6 from Test Example 2, and the liquid crystal emulsion is Example 1 in Test Example 2. The prepared conventional emulsion and liquid crystal emulsion are designated as Comparative Example 5 and Example 1, respectively. The stability of intercellular lipids in a formulation is determined based on a change in viscosity under the conditions of refrigeration, cooling, room temperature and high temperature. Measurement is carried out with a viscometer (Brookfield, DV-1 prime, USA) at room temperature (25° C.) by using spindle No. 64 under the conditions of 30 rpm. Measurement of viscosity is in the unit of cp. Right after the preparation of emulsion and after the lapse of 3 months, the viscosity under each of the storage conditions in a thermostat is listed in the following Table 4.

TABLE 4

| | Refrigeration | | Cooling | | Room temperature | | 45° C. | | CYC | |
|---|---|---|---|---|---|---|---|---|---|---|
| | Right after preparation | After 3 months | Right after preparation | After 3 months | Right after preparation | After 3 months | Right after preparation | After 3 months | Right after preparation | After 3 months |
| Ex. 1 | 9,500 | 10,000 | 9,500 | 10,500 | 9,500 | 10,700 | 9,500 | 11,000 | 9,500 | 10,900 |
| Comp. Ex. 5 | 6,500 | 10,000 | 6,500 | 12,000 | 6,500 | Non-detectable | 6,500 | Non-detectable | 6,500 | Non-detectable |

As shown in Table 4, the liquid crystal emulsion (Example 1) shows an insignificant change in viscosity of 1,000-1,500 cp right after its preparation and after the lapse of 3 months. On the contrary, the conventional emulsion (Comparative Example 5) causes a change in viscosity of 3,500 cp or more under the conditions of refrigeration and cooling right after its preparation and after the lapse of 3 months. Particularly, under the room temperature and high-temperature storage conditions, a rapid increase in viscosity occurs, and thus viscosity cannot be determined.

Test Example 5: Test for Skin Safety of Liquid Crystal Emulsion

Example 1 and Comparative Example 4 are evaluated for a skin irritation degree when applied to ten male and female adults not suffering from skin diseases as subjects. First, 20 µL of each sample is applied to the forearm of each subject. Next, the test site is sealed and is allowed to be covered with a patch for 24 hours. After removing the patch, the reaction on the skin after 30 minutes and 24 hours is examined based on the terminology suggested in the CTFA (Cosmetic, Toiletry and Fragrance Association) Guideline. The evaluation criteria are as follows. The grades obtained from the subjects according to the evaluation criteria are averaged, and then evaluated as low irritative (average<1), slightly irritative (average<3), moderately irritative (average<5) and highly irritative (average 5).

TABLE 5

| Test Item | Ex. 1 | Comp. Ex. 4 |
|---|---|---|
| Skin irritation index (PII) | Non-irritative | Non-irritative |

After the test, as can be seen from Table 5, the liquid crystal emulsion having a multilayer lamellar structure including intercellular lipids according to each of Example 1 and Comparative Example 4 causes no irritation, and thus can be used safely for commercial products.

The invention claimed is:

1. A method for preparing a liquid crystal emulsion, comprising the steps of:
    a) mixing, warming and dissolving intercellular lipid ingredients, non-polyoxyethylene (POE) based non-ionic surfactant, higher fatty alcohol, oil and wax to provide an oil phase part;
    b) mixing, warming and dissolving water, polyol and aqueous phase ingredients to provide an aqueous phase part;
    c) adding the oil phase part to the aqueous phase part, followed by agitation, to form a mixture solution;
    d) introducing a viscosity modifier to the mixture solution, while agitating the mixture solution, to form a modified mixture solution;
    e) subjecting the modified mixture solution to rapid cooling under vacuum, while carrying out debubbling under vacuum, to form a rapid-cooled mixture solution; and
    f) filtering the rapid-cooled mixture solution through a filtering paper or a filtering cloth,
    wherein the non-polyoxyethylene (POE) based non-ionic surfactant in the step (a) is a mixture of lecithin, sorbitan-based surfactants, and glucoside-based surfactants.

2. The method for preparing a liquid crystal emulsion according to claim 1, wherein the intercellular lipids include ceramides, cholesterol, phytosphingosine, triglycerides and free fatty acids.

3. The method for preparing a liquid crystal emulsion according to claim 1, wherein the lecithin is used in an amount of 0.05-1 wt %, the sorbitan-based surfactant is used in an amount of 0.1-5 wt %, and the glucoside-based surfactant is used in an amount of 0.1-5 wt %, based on a total weight of the liquid crystal emulsion.

4. The method for preparing a liquid crystal emulsion according to claim 1, wherein the polyol is at least one selected from the group consisting of glycerin, propylene glycol, dipropylene glycol, 1,3-butylene glycol, pentylene glycol, 1,2-octanediol and 1,2-hexanediol.

5. The method for preparing a liquid crystal emulsion according to claim 1, wherein the rapid cooling is carried out from 70° C.-90° C. to 40-50° C. within 5-15 minutes after forming the modified mixture solution.

6. The method for preparing a liquid crystal emulsion according to claim 1, wherein the liquid crystal emulsion has a multilayer lamellar structure.

* * * * *